United States Patent
Wang et al.

(10) Patent No.: US 7,158,860 B2
(45) Date of Patent: Jan. 2, 2007

(54) HEALTHCARE TELE-ROBOTIC SYSTEM WHICH ALLOWS PARALLEL REMOTE STATION OBSERVATION

(75) Inventors: Yulun Wang, Goleta, CA (US); Charles S. Jordan, Santa Barbara, CA (US); Marco Pinter, Santa Barbara, CA (US); Jonathan Southard, Santa Barbara, CA (US)

(73) Assignee: InTouch Technologies, Inc., Goleta, CA (US)

( * ) Notice: Subject to any disclaimer, the term of this patent is extended or adjusted under 35 U.S.C. 154(b) by 91 days.

(21) Appl. No.: 10/660,862

(22) Filed: Sep. 12, 2003

(65) Prior Publication Data

US 2004/0167666 A1 Aug. 26, 2004

Related U.S. Application Data

(60) Provisional application No. 60/449,763, filed on Feb. 24, 2003.

(51) Int. Cl.
*G06F 19/00* (2006.01)

(52) U.S. Cl. ............... 700/245; 700/247; 700/248; 700/251; 700/257; 700/258; 700/259; 700/260; 700/261; 700/262; 700/264; 318/568.11; 318/568.13; 318/568.16; 318/568.21; 318/568.25; 606/1; 606/102; 606/130; 606/139; 600/117; 600/118; 600/407; 600/426; 600/429; 600/587; 600/595; 901/1; 901/2; 901/27

(58) Field of Classification Search ........ 700/131–132, 700/245–248, 251, 253, 257–262, 264; 606/1, 606/102, 130, 139; 318/568.11, 568.12, 318/568.13, 568.16, 568.21, 568.22, 568.25; 600/102–103, 109, 117–118, 407, 426, 429, 600/587, 595; 901/1–2, 27, 36
See application file for complete search history.

(56) References Cited

U.S. PATENT DOCUMENTS

| | | | |
|---|---|---|---|
| 5,374,879 A | 12/1994 | Pin et al. | |
| 5,802,494 A * | 9/1998 | Kuno | 705/2 |
| 5,959,423 A | 9/1999 | Nakanishi et al. | |
| 6,259,806 B1 | 7/2001 | Green | |
| 6,292,713 B1 | 9/2001 | Jouppi et al. | |
| 6,346,950 B1 | 2/2002 | Jouppi | |
| 6,369,847 B1 | 4/2002 | James et al. | |

(Continued)

FOREIGN PATENT DOCUMENTS

CA 2289697 A1 11/1998

OTHER PUBLICATIONS

☐☐Mack, Minimally invasive and robotic surgery, 2001, IEEE, pp. 568-572.*

(Continued)

*Primary Examiner*—Thomas Black
*Assistant Examiner*—McDieunel Marc
(74) *Attorney, Agent, or Firm*—Ben J. Yorks; Irell & Manella LLP

(57) ABSTRACT

A robotic system that includes a mobile robot linked to a plurality of remote stations. The robot provides both audio and visual information to the stations. One of the remote stations, a primary station, may control the robot while receiving and providing audio and visual information with the remote controlled robot. The other stations, the secondary stations, may also receive the audio and visual information transmitted between the robot and the primary station. This allows operators of the secondary stations to observe, communicate and be trained through the robot and primary station. Such an approach may reduce the amount of travel required to train personnel.

36 Claims, 10 Drawing Sheets

U.S. PATENT DOCUMENTS

| | | | |
|---|---|---|---|
| 6,430,471 | B1 | 8/2002 | Kintou et al. |
| 6,463,361 | B1 | 10/2002 | Wang et al. |
| 6,491,701 | B1 | 12/2002 | Tierney et al. |
| 6,496,099 | B1 | 12/2002 | Wang et al. |
| 6,522,906 | B1 * | 2/2003 | Salisbury et al. ........... 600/407 |
| 6,535,793 | B1 | 3/2003 | Allard |
| 6,549,215 | B1 | 4/2003 | Jouppi |
| 6,587,750 | B1 * | 7/2003 | Gerbi et al. ................ 700/245 |
| 6,594,552 | B1 * | 7/2003 | Nowlin et al. .............. 700/260 |
| 6,684,129 | B1 * | 1/2004 | Salisbury et al. ........... 700/245 |
| 6,785,593 | B1 * | 8/2004 | Wang et al. ................ 700/258 |
| 6,799,065 | B1 * | 9/2004 | Niemeyer ................... 600/407 |
| 6,799,088 | B1 * | 9/2004 | Wang et al. ................ 700/258 |
| 6,836,703 | B1 * | 12/2004 | Wang et al. ................ 700/258 |
| 6,839,612 | B1 * | 1/2005 | Sanchez et al. ............. 700/245 |
| 6,852,107 | B1 * | 2/2005 | Wang et al. .................... 606/1 |
| 6,871,117 | B1 * | 3/2005 | Wang et al. ................ 700/245 |
| 6,892,112 | B1 * | 5/2005 | Wang et al. ................ 700/258 |
| 2001/0054071 | A1 | 12/2001 | Loeb |
| 2002/0027597 | A1 | 3/2002 | Sachau |
| 2002/0057279 | A1 | 5/2002 | Jouppi |
| 2002/0058929 | A1 | 5/2002 | Green |
| 2002/0063726 | A1 | 5/2002 | Jouppi |
| 2002/0120362 | A1 | 8/2002 | Lathan et al. |
| 2002/0130950 | A1 | 9/2002 | James et al. |
| 2002/0141595 | A1 | 10/2002 | Jouppi |
| 2002/0183894 | A1 | 12/2002 | Wang et al. |
| 2003/0050733 | A1 | 3/2003 | Wang et al. |
| 2003/0114962 | A1 * | 6/2003 | Niemeyer ................... 700/245 |
| 2003/0135203 | A1 * | 7/2003 | Wang et al. .................... 606/1 |
| 2003/0144649 | A1 * | 7/2003 | Ghodoussi et al. ............ 606/1 |
| 2003/0151658 | A1 | 8/2003 | Smith |
| 2003/0220541 | A1 * | 11/2003 | Salisbury et al. ........... 600/101 |
| 2005/0038416 | A1 * | 2/2005 | Wang et al. .................... 606/1 |
| 2006/0047365 | A1 * | 3/2006 | Ghodoussi et al. ......... 700/251 |

OTHER PUBLICATIONS

Davies, Rototics in minimilly invasive surgery, 1995, Internet, pp. 5/1-5/2.*

Stoianovici et al., rototic tools for minimally invasive urologic surgery, 2002, Internet, 1-17.*

Tendick et al., Human-machine interfaces for minimally invasive surgery, 1997, IEEE, pp. 1-6.*

Schaaf, Robotic surgery: The future in now, 2001, Internet, pp. 1-11.*

Student BMJ, Robotics in surgery, 2002, Internet, pp. 1-4.*

Hopkinsmedicine, Dr. Robot Tested at Hpkins, 2002, Internet, p. 1-2.*

Paulos et al., "A World Wide Web Telerobotic Remote Environment Browser", http://vive.cs.berkeley.edu/capek, 1995.

Telepresence Research, Inc., "Telepresence Mobile Robot System", http://www.telepresence.com/telepresence-research/TELEROBOT/, Feb. 20, 1995.

Zorn, Benjamin G., "Ubiquitous Telepresence", http://www.cs.colorado.edu/~zom/ut/vision.html, Mar. 5, 1996.

Paulos, et al., "Ubiquitous Tele-embodiment: Applications and Implications", International Journal of Human Computer Studies, Jun. 1997, vol. 46, No. 6, pp. 861-877.

Paulos, et al., "Designing Personal Tele-Embodiment", Presented at the IEEE International Conference on Robotics and Animation, Leuven, Belgium, May 20, 1998.

Harmo et al., "Moving Eye—Interactive Telepresence Over Internet With a Ball Shaped Mobile Robot", 2000.

Loeb, Gerald, "Virtual Visit: Improving Communication for Those Who Need It Most", 2001.

Paulos, Eric John, "Personal Tele-Embodiment", 2001.

Hees, William P., "Communications Design for a Remote Presence Robot", Jan. 14, 2002.

Jacobs et al., "TeleRehab: Applying Telemedicine to Outpatient Physical Therapy", 2002.

Jouppi, et al., :Mutually-Immersive Audio Telepresence, Audio Engineering Society Convention Paper, presented at 113th Convention Oct. 2002.

Jouppi, Norman P., "First Steps Towards Mutually-Immersive Mobile Telepresence", 2002.

Bauer, Jeffrey C., "Service Robots in Health Care: The Evolution of Mechanical Solutions to Human Resource Problems", Jun. 2003.

* cited by examiner

US 7,158,860 B2

HEALTHCARE TELE-ROBOTIC SYSTEM WHICH ALLOWS PARALLEL REMOTE STATION OBSERVATION

REFERENCE TO CROSS-RELATED APPLICATIONS

This application claims priority to Provisional Application No. 60/449,763 filed on Feb. 24, 2003.

BACKGROUND OF THE INVENTION

1. Field of the Invention

The subject matter disclosed generally relates to the field of robotics.

2. Background Information

There is a growing need to provide remote health care to patients that have a variety of ailments ranging from Alzheimers to stress disorders. To minimize costs it is desirable to provide home care for such patients. Home care typically requires a periodic visit by a health care provider such as a nurse or some type of assistant. Due to financial and/or staffing issues the health care provider may not be there when the patient needs some type of assistance. Additionally, existing staff must be continuously trained, which can create a burden on training personnel. It would be desirable to provide a system that would allow a health care provider to remotely care for a patient without being physically present.

Robots have been used in a variety of applications ranging from remote control of hazardous material to assisting in the performance of surgery. For example, U.S. Pat. No. 5,762, 458 issued to Wang et al. discloses a system that allows a surgeon to perform minimally invasive medical procedures through the use of robotically controlled instruments. One of the robotic arms in the Wang system moves an endoscope which has a camera that allows a surgeon to view a surgical area of a patient.

Tele-robots such as hazardous waste handlers and bomb detectors may contain a camera that allows the operator to view the remote site. Canadian Pat. No. 2289697 issued to Treviranus, et al. discloses a teleconferencing platform that has both a camera and a monitor. The Tetravirus patent also discloses embodiments with a mobile platform, and different mechanisms for moving the camera and the monitor.

Publication Application No. US-2003-0050233-A1 discloses a remote robotic system wherein a plurality of remote stations can control a plurality of robotic arms used to perform a minimally invasive medical procedure. Each remote station can receive a video image provided by the endoscope inserted into the patient. Such a system is also being developed by Computer Motion, Inc. under the name SOCRATES. The remote stations are linked to the robotic system by a dedicated communication link.

BRIEF SUMMARY OF THE INVENTION

A mobile robotic system that includes a mobile robot coupled to a first remote station and a second remote station. Movement of the mobile robot is controlled through the first remote station. The mobile robot has a camera that captures a video image. The first and second remote stations both receive the video image.

DETAILED DESCRIPTION

Disclosed is a robotic system that includes a mobile robot linked to a plurality of remote stations. The robot provides both audio and visual information to the stations. One of the remote stations, a primary station, may control the robot while receiving and providing audio and visual information with the remote controlled robot. The other stations, the secondary stations, may also receive the audio and visual information transmitted between the robot and the primary station. This allows operators of the secondary stations to observe and be trained through the robot and primary station. Such an approach may reduce the amount of travel required to train personnel. For example, a nurse may instruct other personnel on how to care for a special need patient. The secondary station operators can observe a training season through the "eyes" of the robot.

Figure 1:
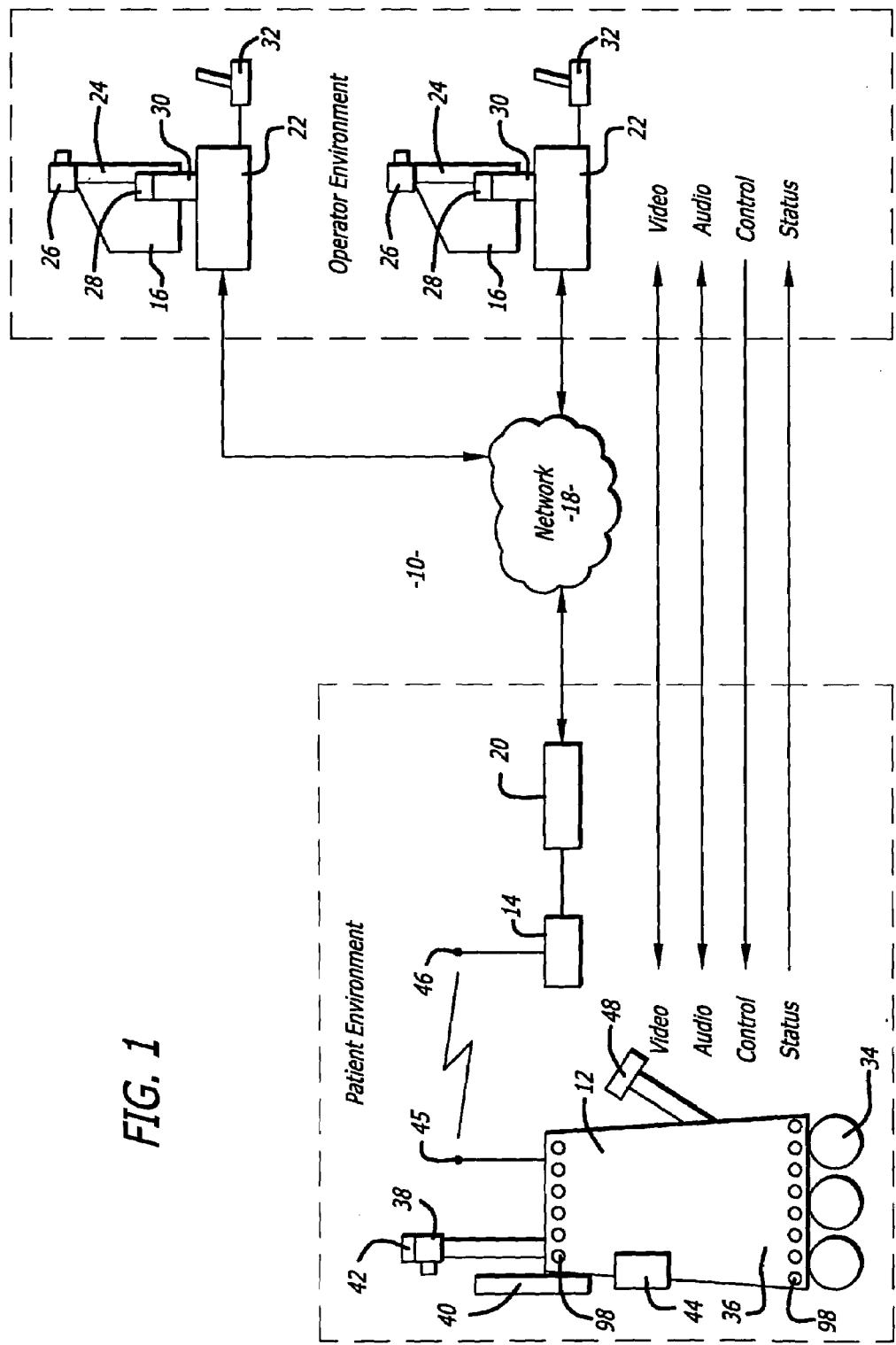
FIG. 1 is an illustration of a robotic system.

Referring to the drawings more particularly by reference numbers, FIG. 1 shows a robotic system 10. The robotic system 10 includes a robot 12, a base station 14 and a plurality of remote control stations 16. Each remote control station 16 may be coupled to the base station 14 through a network 18. By way of example, the network 18 may be either a packet switched network such as the Internet, or a circuit switched network such has a Public Switched Telephone Network (PSTN) or other broadband system. The base station 14 may be coupled to the network 18 by a modem 20 or other broadband network interface device.

Each remote control station 16 may include a computer 22 that has a monitor 24, a camera 26, a microphone 28 and a speaker 30. The computer 22 may also contain an input device 32 such as a joystick or a mouse. Each control station 16 is typically located in a place that is remote from the robot 12. Although only one robot 12 is shown, it is to be understood that the system 10 may have a plurality of robots 12. In general any number of robots 12 may be controlled by any number of remote stations. For example, one remote station 16 may be coupled to a plurality of robots 12, or one robot 12 may be coupled to a plurality of remote stations 16.

The robot 12 includes a movement platform 34 that is attached to a robot housing 36. Also attached to the robot housing 36 are a camera 38, a monitor 40, a microphone(s) 42 and a speaker 44. The microphone 42 and speaker 30 may create a stereophonic sound. The robot 12 may also have an antenna 45 that is wirelessly coupled to an antenna 46 of the base station 14. The system 10 allows a user at the remote control station 16 to move the robot 12 through the input device 32. The robot camera 38 is coupled to the remote monitor 24 so that a user at the remote station 16 can view a patient. Likewise, the robot monitor 40 is coupled to the remote camera 26 so that the patient can view the user. The microphones 28 and 42, and speakers 30 and 44, allow for audible communication between the patient and the user. The robot 12 may further have a handle 48 that can be rotated to a down position which allows someone to manually push or pull the robot 12.

Each remote station computer 22 may operate Microsoft OS software and WINDOWS XP or other operating systems such as LINUX. The remote computer 22 may also operate a video driver, a camera driver, an audio driver and a joystick driver. The video images may be transmitted and received with compression software such as MPEG CODEC.

Figure 2:
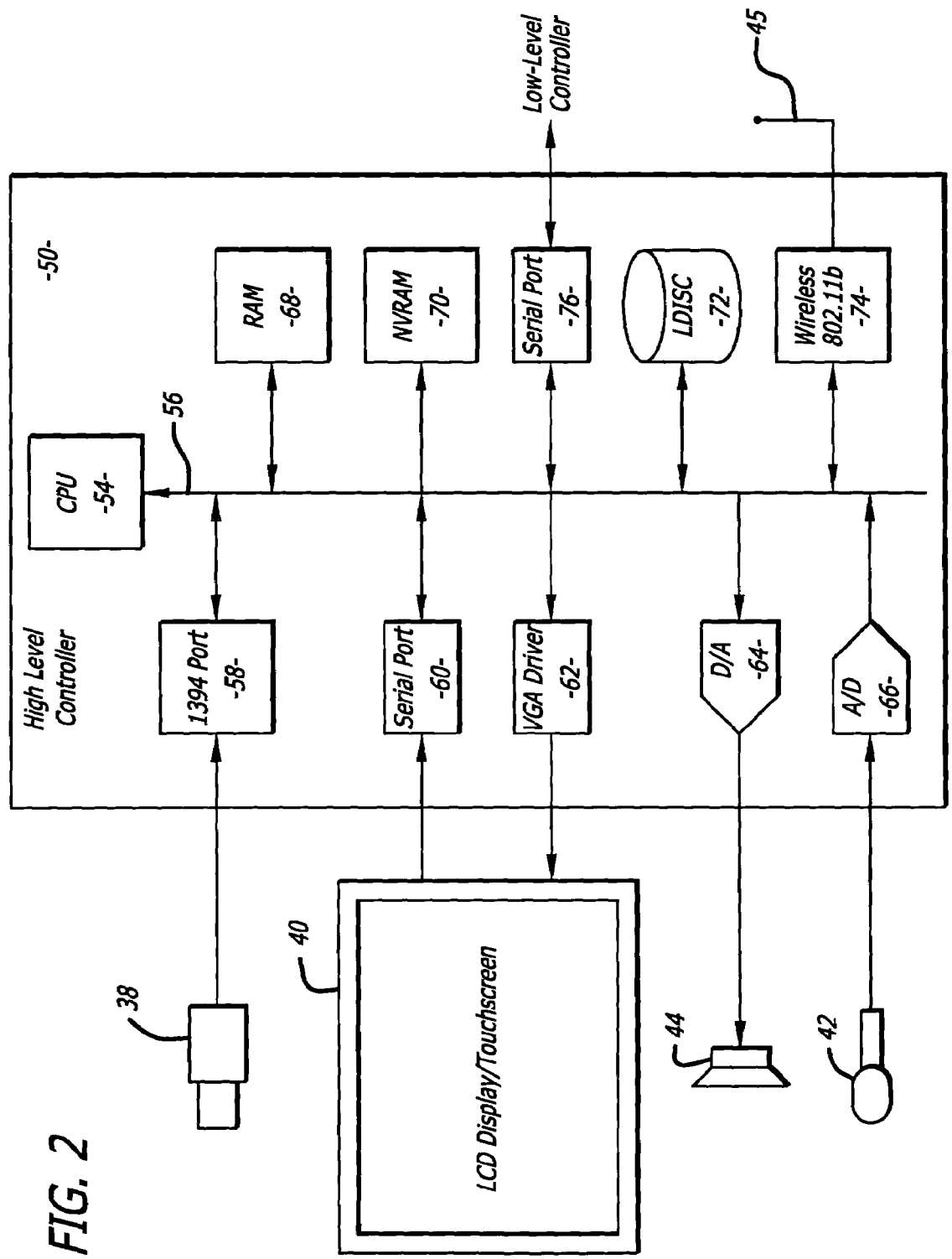
FIG. 2 is a schematic of an electrical system of a robot.
Figure 3:
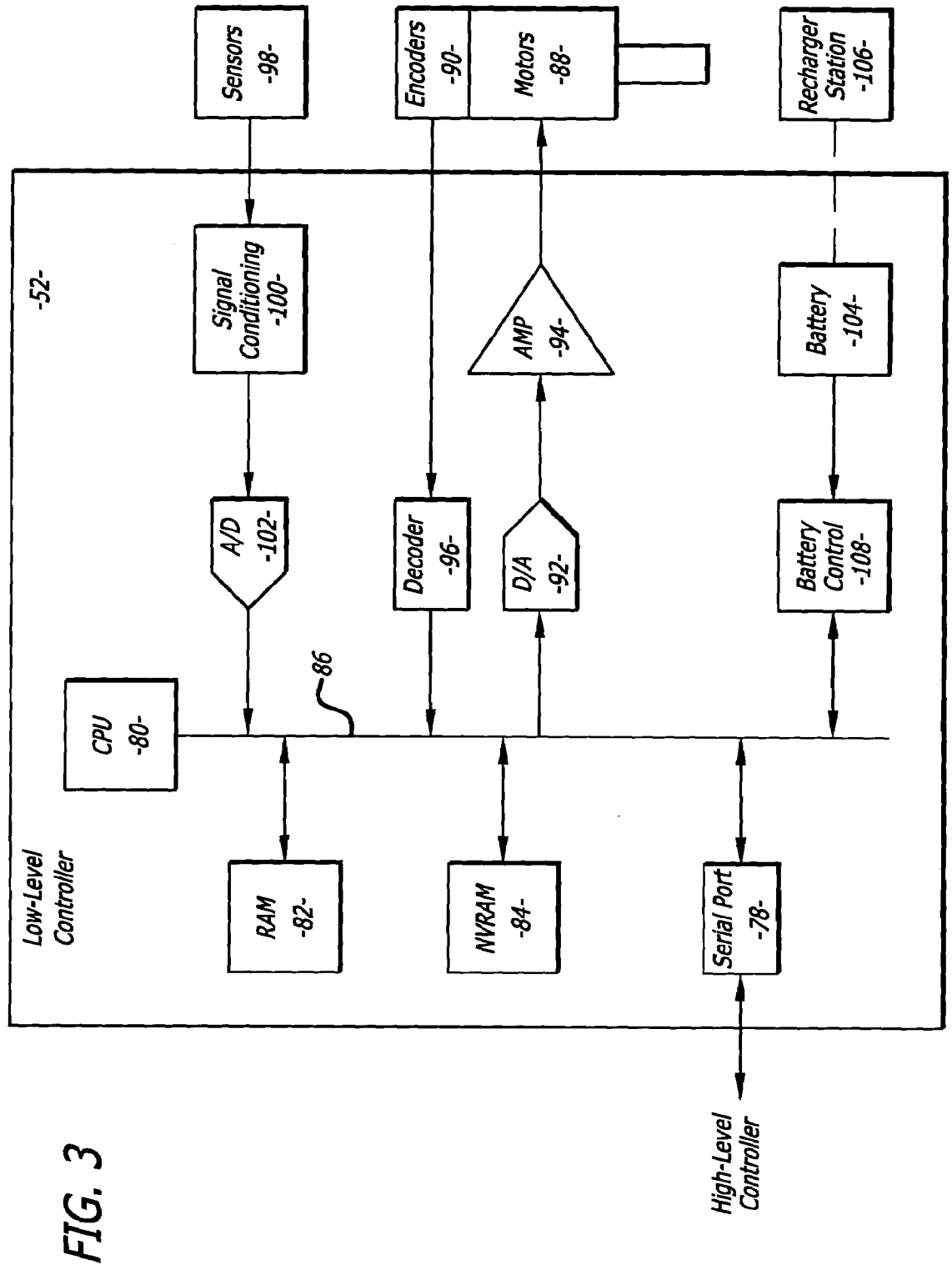
FIG. 3 is a further schematic of the electrical system of the robot.

FIGS. 2 and 3 show an embodiment of the robot 12. The robot 12 may include a high level control system 50 and a low level control system 52. The high level control system 50 may include a processor 54 that is connected to a bus 56. The bus is coupled to the camera 38 by an input/output (I/O) port 58, and to the monitor 40 by a serial output port 60 and a VGA driver 62. The monitor 40 may include a touchscreen function that allows the patient to enter input by touching the monitor screen.

The speaker 44 is coupled to the bus 56 by a digital to analog converter 64. The microphone 42 is coupled to the bus 56 by an analog to digital converter 66. The high level controller 50 may also contain random access memory (RAM) device 68, a non-volatile RAM device 70 and a mass storage device 72 that are all coupled to the bus 62. The mass storage device 72 may contain medical files of the patient that can be accessed by the user at the remote control station 16. For example, the mass storage device 72 may contain a picture of the patient. The user, particularly a health care provider, can recall the old picture and make a side by side comparison on the monitor 24 with a present video image of the patient provided by the camera 38. The robot antennae 45 may be coupled to a wireless transceiver 74. By way of example, the transceiver 74 may transmit and receive information in accordance with IEEE 802.11b.

The controller 54 may operate with a LINUX OS operating system. The controller 54 may also operate MS WINDOWS along with video, camera and audio drivers for communication with the remote control station 16. Video information may be transceived using MPEG CODEC compression techniques. The software may allow the user to send e-mail to the patient and vice versa, or allow the patient to access the Internet. In general the high level controller 50 operates to control the communication between the robot 12 and the remote control station 16.

The high level controller 50 may be linked to the low level controller 52 by serial ports 76 and 78. The low level controller 52 includes a processor 80 that is coupled to a RAM device 82 and non-volatile RAM device 84 by a bus 86. The robot 12 contains a plurality of motors 88 and motor encoders 90. The encoders 90 provide feedback information regarding the output of the motors 88. The motors 88 can be coupled to the bus 86 by a digital to analog converter 92 and a driver amplifier 94. The encoders 90 can be coupled to the bus 86 by a decoder 96. The robot 12 also has a number of proximity sensors 98 (see also FIG. 1). The position sensors 98 can be coupled to the bus 86 by a signal conditioning circuit 100 and an analog to digital converter 102.

The low level controller 52 runs software routines that mechanically actuate the robot 12. For example, the low level controller 52 provides instructions to actuate the movement platform to move the robot 12. The low level controller 52 may receive movement instructions from the high level controller 50. The movement instructions may be received as movement commands from the remote control station. Although two controllers are shown, it is to be understood that the robot 12 may have one controller controlling the high and low level functions.

The various electrical devices of the robot 12 may be powered by a battery(ies) 104. The battery 104 may be recharged by a battery recharger station 106 (see also FIG. 1). The low level controller 52 may include a battery control circuit 108 that senses the power level of the battery 104. The low level controller 52 can sense when the power falls below a threshold and then send a message to the high level controller 50. The high level controller 50 may include a power management software routine that causes the robot 12 to move so that the battery 104 is coupled to the recharger 106 when the battery power falls below a threshold value. Alternatively, the user can direct the robot 12 to the battery recharger 106. Additionally, the battery 104 may be replaced or the robot 12 may be coupled to a wall power outlet by an electrical cord (not shown).

Figure 4:
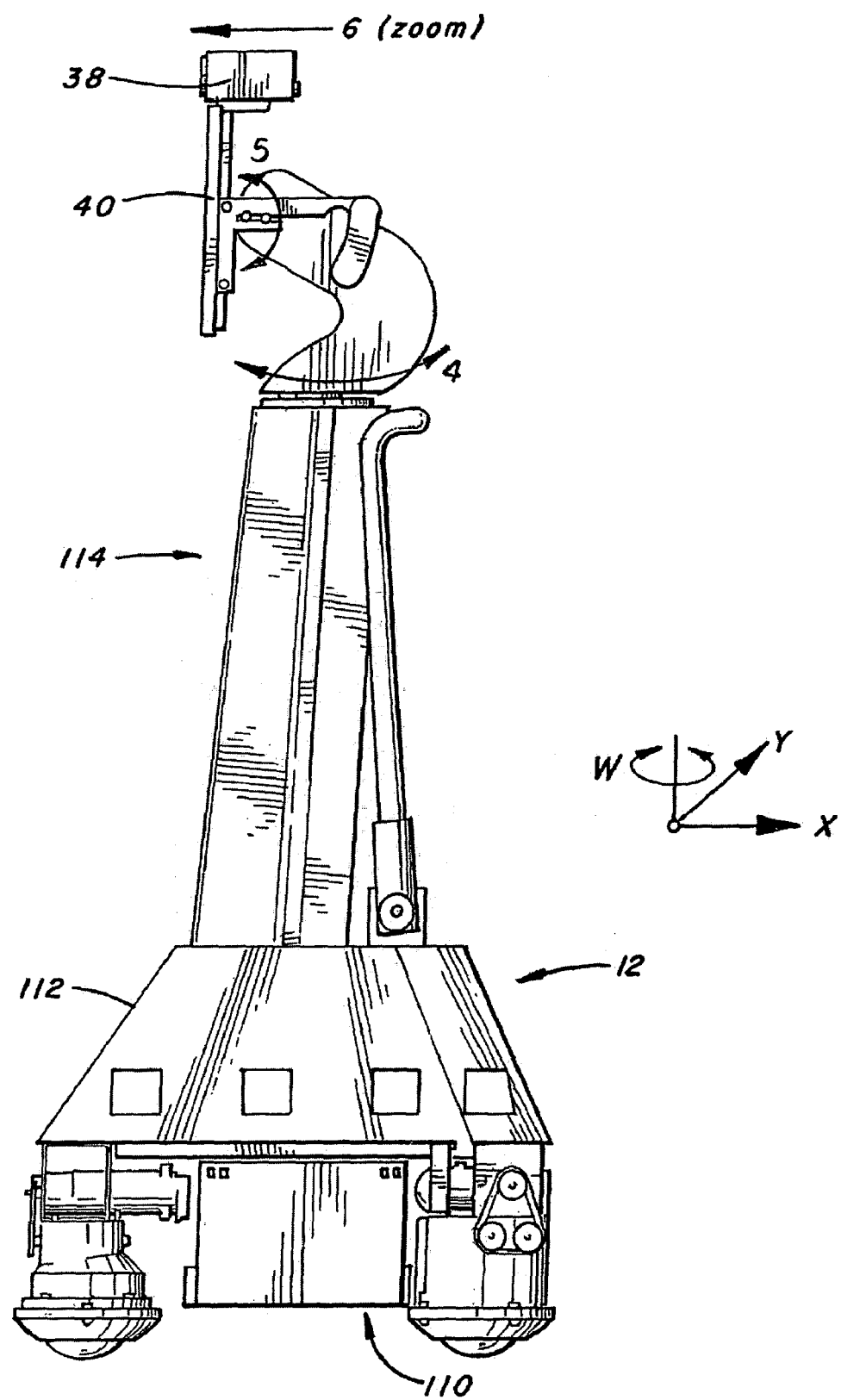
FIG. 4 is side view of the robot.

FIG. 4 shows an embodiment of the robot 12. The robot 12 may include a holonomic platform 110 that is attached to a robot housing 112. The holonomic platform 110 provides three degrees of freedom to allow the robot 12 to move in any direction.

The robot 12 may have an pedestal assembly 114 that supports the camera 38 and the monitor 40. The pedestal assembly 114 may have two degrees of freedom so that the camera 26 and monitor 24 can be swiveled and pivoted as indicated by the arrows.

Figure 5:
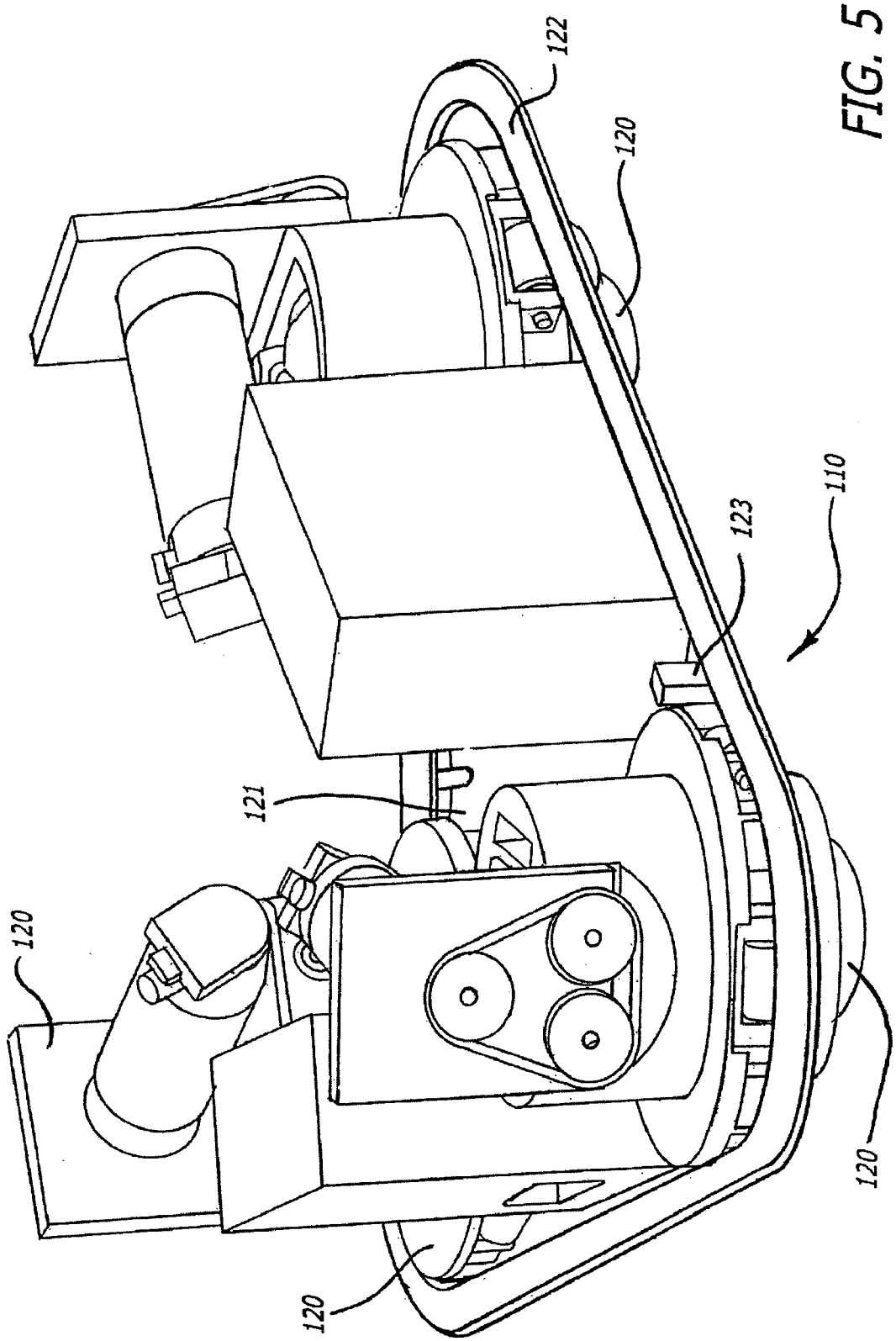
FIG. 5 is a top perspective view of a holonomic platform of the robot.

As shown in FIG. 5 the holonomic platform 110 may include three roller assemblies 120 that are mounted to a base plate 121. The roller assemblies 120 are typically equally spaced about the platform 110 and allow for movement in any direction, although it is to be understood that the assemblies may not be equally spaced.

The robot housing 112 may include a bumper 122. The bumper 122 may be coupled to optical position sensors 123 that detect when the bumper 122 has engaged an object. After engagement with the object the robot can determine the direction of contact and prevent further movement into the object.

Figure 6:
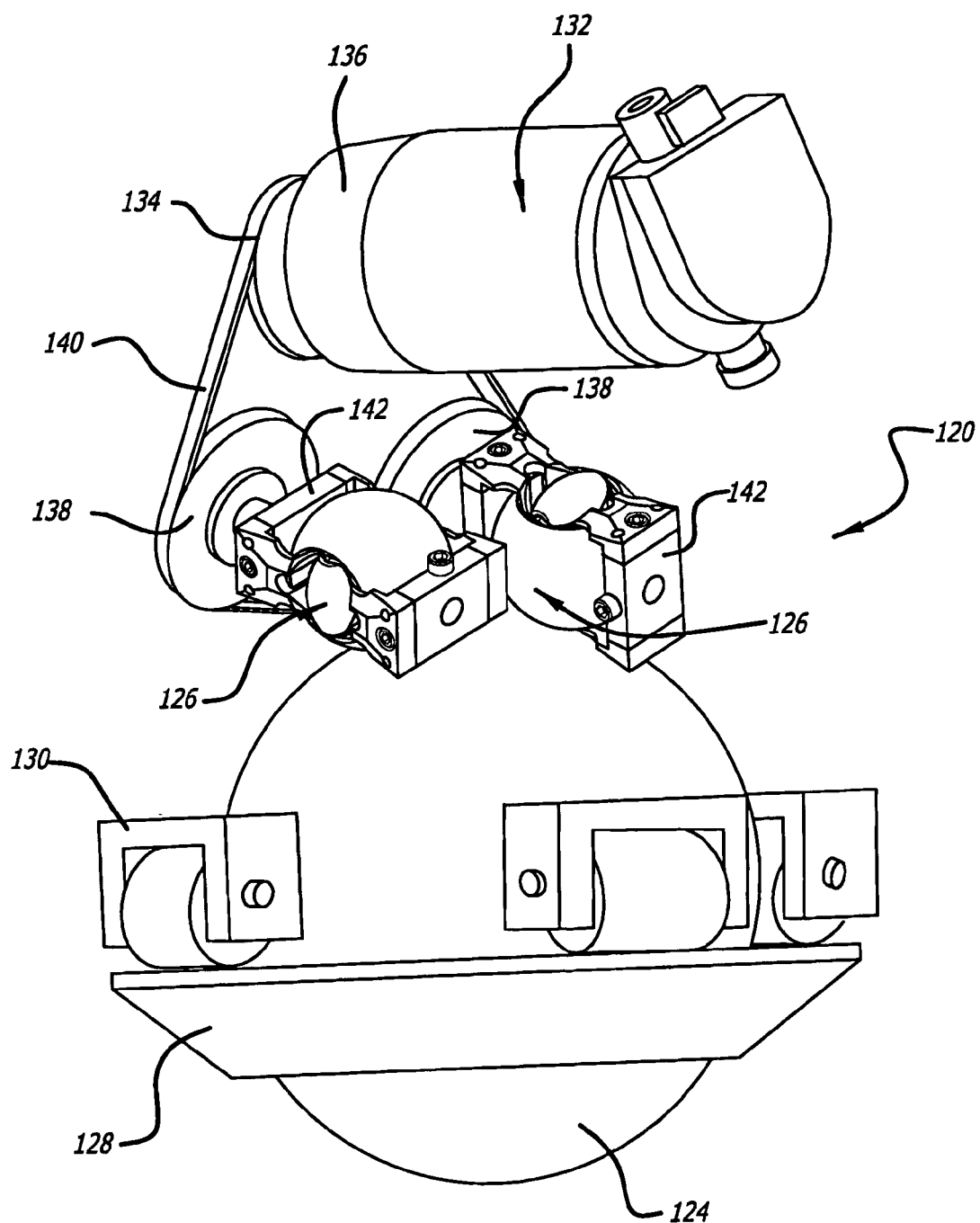
FIG. 6 is a side perspective view of a roller assembly of the holonomic platform.

FIG. 6 shows an embodiment of a roller assembly 120. Each assembly 120 may include a drive ball 124 that is driven by a pair of transmission rollers 126. The assembly 120 may include a retainer ring 128 and a plurality of bushings 130 that captures and allows the ball 124 to rotate in an x and y direction but prevents movement in a z direction. The assembly also holds the ball under the transmission rollers 126.

The transmission rollers 126 are coupled to a motor assembly 132. The assembly 132 corresponds to the motor 88 shown in FIG. 3. The motor assembly 132 includes an output pulley 134 attached to a motor 136. The output pulley 134 is coupled to a pair of ball pulleys 138 by a drive belt 140. The ball pulleys 138 are each attached to a transmission bracket 142. The transmission rollers 126 are attached to the transmission brackets 142.

Rotation of the output pulley 134 rotates the ball pulleys 138. Rotation of the ball pulleys 138 causes the transmission rollers 126 to rotate and spin the ball 124 through frictional forces. Spinning the ball 124 will move the robot 12. The transmission rollers 126 are constructed to always be in contact with the drive ball 124. The brackets 142 allow the transmission rollers 126 to freely spin and allow orthogonal directional passive movement of 124 when one of the other roller assemblies 120 is driving and moving the robot 12.

Figure 7:
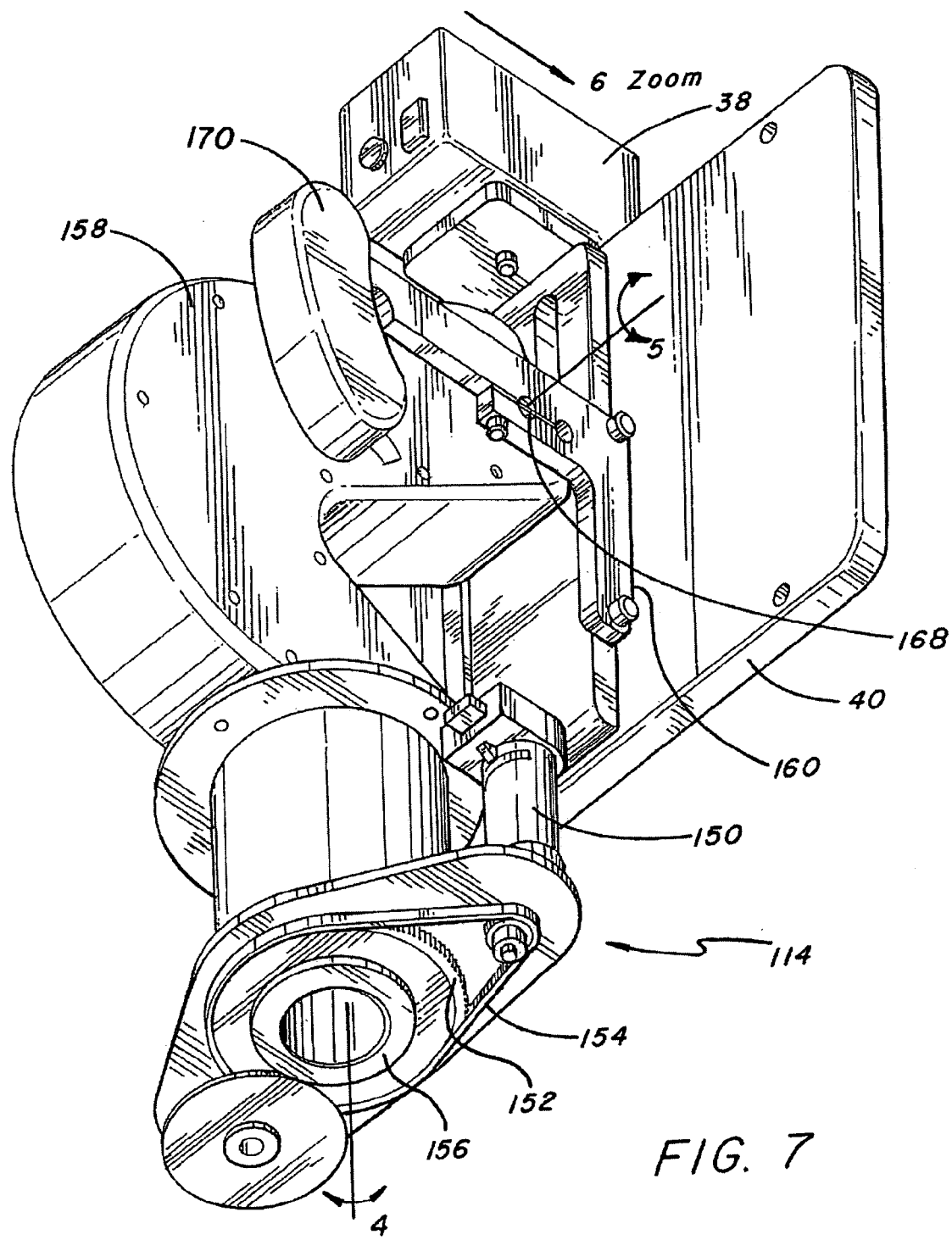
FIG. 7 is a bottom perspective view showing a pedestal assembly of the robot.

As shown in FIG. 7, the pedestal assembly 114 may include a motor 150 that is coupled to a gear 152 by a belt 154. The gear 152 is attached to a shaft 156. The shaft 156 is attached to an arm 158 that is coupled to the camera 38 and monitor 40 by a bracket 160. Activation of the motor 150 rotates the gear 152 and sleeve 156, and causes the camera 38 and monitor 40 to swivel (see also FIG. 4) as indicated by the arrows 4.

Figure 8:
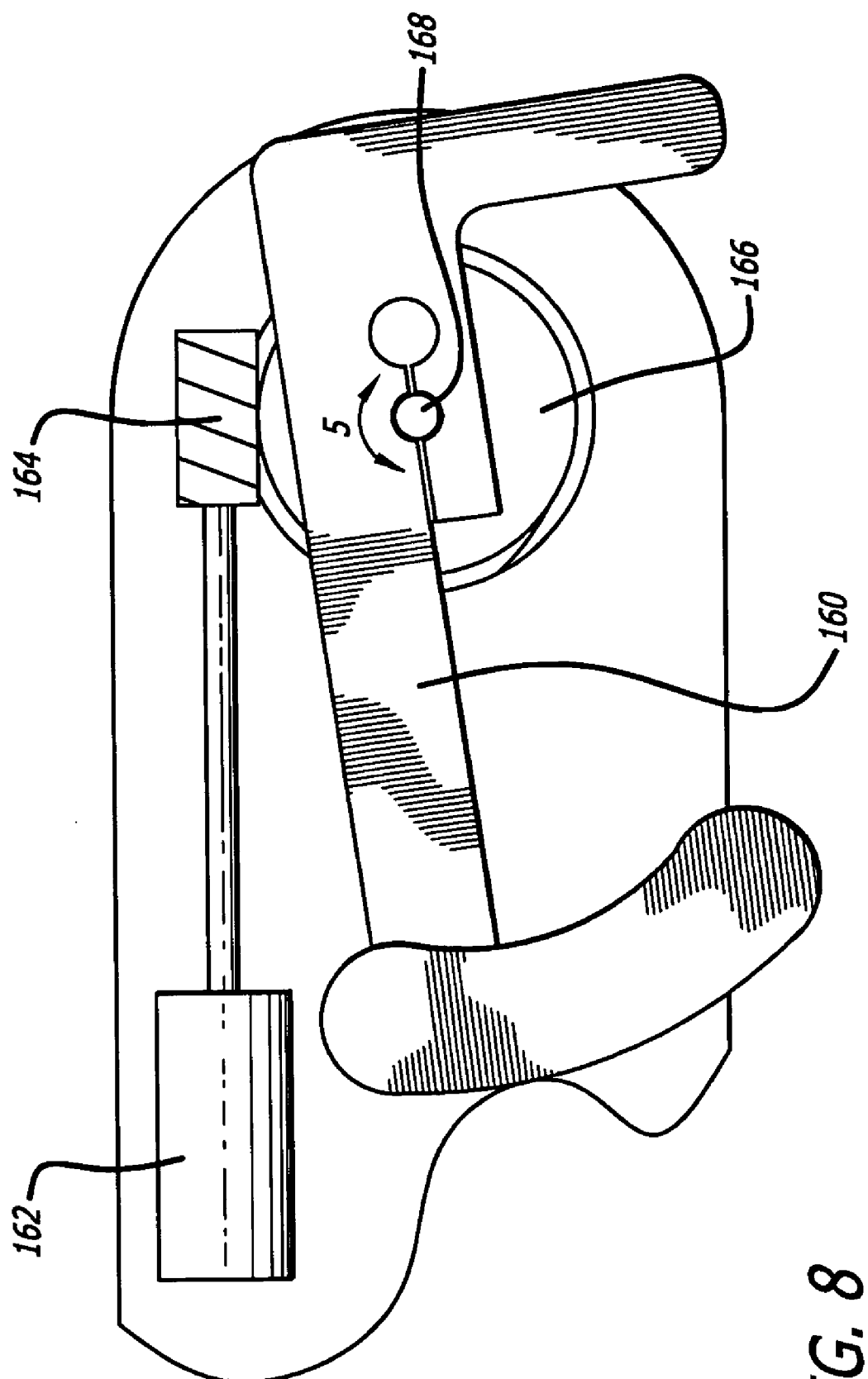
FIG. 8 is a sectional view showing an actuator of the pedestal assembly.

As shown in FIG. 8, the assembly 114 may further include a tilt motor 162 within the arm 158 that can cause the monitor 40 and camera 38 to pivot as indicated by the arrows 5. The tilt motor 162 may rotate a worm 164 that rotates a worm gear 166. The pin 168 is rigidly attached to both the worm gear 166 and the bracket 160 so that rotation of the gear 166 pivots the camera 38 and the monitor 40. The camera 38 may also include a zoom feature to provide yet another degree of freedom for the operator.

In operation, the robot 12 may be placed in a home or a facility where one or more patients are to be monitored and/or assisted. The facility may be a hospital or a residential care facility. By way of example, the robot 12 may be placed in a home where a health care provider may monitor and/or assist the patient. Likewise, a friend or family member may communicate with the patient. The cameras and monitors at both the robot and remote control stations allow for teleconferencing between the patient and the person at the remote station(s).

The robot 12 can be maneuvered through the home or facility by manipulating the input device 32 at a remote station 16.

The robot 10 may be controlled by a number of different users. To accommodate for this the robot may have an arbitration system. The arbitration system may be integrated into the operating system of the robot 12. For example, the arbitration technique may be embedded into the operating system of the high-level controller 50.

By way of example, the users may be divided into classes that include the robot itself, a local user, a caregiver, a doctor, a family member, or a service provider. The robot 12 may override input commands that conflict with robot operation. For example, if the robot runs into a wall, the system may ignore all additional commands to continue in the direction of the wall. A local user is a person who is physically present with the robot. The robot could have an input device that allows local operation. For example, the robot may incorporate a voice recognition system that receives and interprets audible commands.

A caregiver is someone who remotely monitors the patient. A doctor is a medical professional who can remotely control the robot and also access medical files contained in the robot memory. The family and service users remotely access the robot. The service user may service the system such as by upgrading software, or setting operational parameters.

Message packets may be transmitted between a robot 12 and a remote station 16. The packets provide commands and feedback. Each packet may have multiple fields. By way of example, a packet may include an ID field a forward speed field, an angular speed field, a stop field, a bumper field, a sensor range field, a configuration field, a text field and a debug field.

The identification of remote users can be set in an ID field of the information that is transmitted from the remote control station 16 to the robot 12. For example, a user may enter a user ID into a setup table in the application software run by the remote control station 16. The user ID is then sent with each message transmitted to the robot.

The robot 12 may operate in one of two different modes; an exclusive mode, or a sharing mode. In the exclusive mode only one user has access control of the robot. The exclusive mode may have a priority assigned to each type of user. By way of example, the priority may be in order of local, doctor, caregiver, family and then service user. In the sharing mode two or more users may share access with the robot. For example, a caregiver may have access to the robot, the caregiver may then enter the sharing mode to allow a doctor to also access the robot. Both the caregiver and the doctor can conduct a simultaneous teleconference with the patient.

The arbitration scheme may have one of four mechanisms; notification, timeouts, queue and call back. The notification mechanism may inform either a present user or a requesting user that another user has, or wants, access to the robot. The timeout mechanism gives certain types of users a prescribed amount of time to finish access to the robot. The queue mechanism is an orderly waiting list for access to the robot. The call back mechanism informs a user that the robot can be accessed. By way of example, a family user may receive an e-mail message that the robot is free for usage. Tables 1 and 2, show how the mechanisms resolve access request from the various users.

TABLE I

| User | Access Control | Medical Record | Command Override | Software/Debug Access | Set Priority |
| --- | --- | --- | --- | --- | --- |
| Robot | No | No | Yes (1) | No | No |
| Local | No | No | Yes (2) | No | No |
| Caregiver | Yes | Yes | Yes (3) | No | No |
| Doctor | No | Yes | No | No | No |
| Family | No | No | No | No | No |
| Service | Yes | No | Yes | Yes | Yes |

TABLE II

| | | Requesting User | | | | |
| --- | --- | --- | --- | --- | --- | --- |
| | | Local | Caregiver | Doctor | Family | Service |
| Current User | Local | Not Allowed | Warn current user of pending user Notify requesting user that system is in use Set timeout | Warn current user of pending user Notify requesting user that system is in use Set timeout = 5 m | Warn current user of pending user Notify requesting user that system is in use Set timeout = 5 m Call back | Warn current user of pending user Notify requesting user that system is in use No timeout Call back |
| | Caregiver | Warn current user of pending user. Notify requesting | Not Allowed | Warn current user of pending user Notify requesting user | Warn current user of pending user Notify requesting user | Warn current user of pending user Notify requesting |

TABLE II-continued

| | Requesting User | | | | |
| --- | --- | --- | --- | --- | --- |
| | Local | Caregiver | Doctor | Family | Service |
| | user that system is in use. Release control | | that system is in use Set timeout = 5 m Queue or callback | that system is in use Set timeout = 5 m | user that system is in use No timeout Callback |
| Doctor | Warn current user of pending user Notify requesting user that system is in use Release control | Warn current user of pending user Notify requesting user that system is in use Set timeout = 5 m | Warn current user of pending user Notify requesting user that system is in use No timeout Callback | Notify requesting user that system is in use No timeout Queue or callback | Warn current user of pending user Notify requesting user that system is in use No timeout Callback |
| Family | Warn current user of pending user Notify requesting user that system is in use Release Control | Notify requesting user that system is in use No timeout Put in queue or callback | Warn current user of pending user Notify requesting user that system is in use Set timeout = 1 m | Warn current user of pending user Notify requesting user that system is in use Set timeout = 5 m Queue or callback | Warn current user of pending user Notify requesting user that system is in use No timeout Callback |
| Service | Warn current user of pending user Notify requesting user that system is in use No timeout | Notify requesting user that system is in use No timeout Callback | Warn current user of request Notify requesting user that system is in use No timeout Callback | Warn current user of pending user Notify requesting user that system is in use No timeout Queue or callback | Not Allowed |

The information transmitted between the station 16 and the robot 12 may be encrypted. Additionally, the user may have to enter a password to enter the system 10. A selected robot is then given an electronic key by the station 16. The robot 12 validates the key and returns another key to the station 16. The keys are used to encrypt information transmitted in the session.

Figure 9:
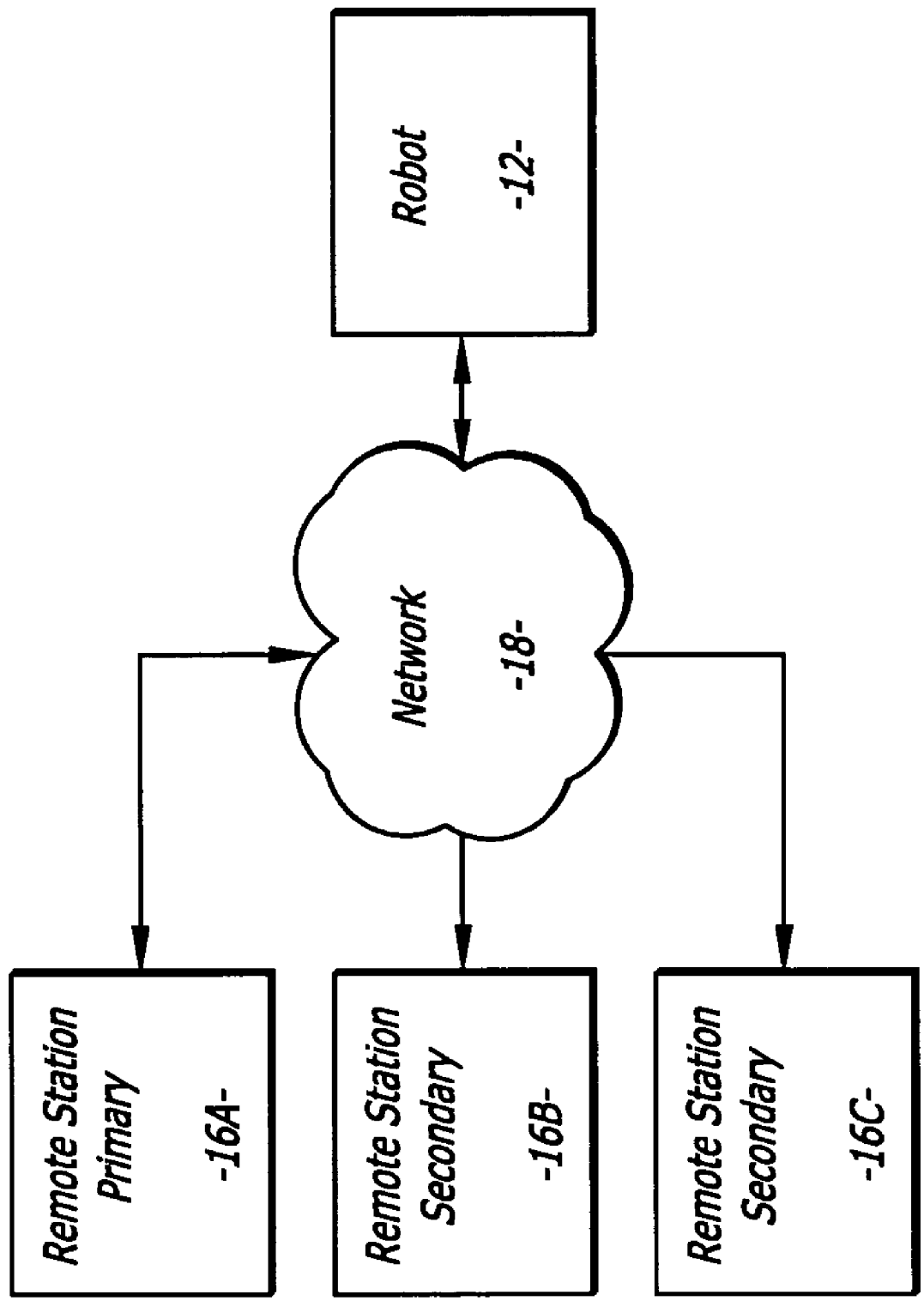
FIG. 9 is a schematic of a robotic system wherein multiple remote stations are coupled to the robot.

FIG. 9 shows a system with a plurality of remote stations 16A, 16B and 16C that can access a robot 12 through a network 18. The system can be set into an active plus observational mode wherein one primary remote station 16A controls movement of the robot and receives both audio and visual information from the robot camera and speaker, respectively. The secondary stations 16B and 16C also receive audio and visual information transmitted between the robot 12 and the station 16A. This mode allows multiple users at stations 16B and 16C to observe use of the robot while a teacher or master at station 16A moves the robot.

The observational mode can be set through a graphical user interface of the primary remote station 16A. The primary remote station 16A can retransmit the audio/visual information received from the robot 12 to the secondary stations 16B and 16C. This can be done by changing the ID(s) in the ID field of the data packets received from the robot and then retransmitting the packets to the secondary stations. Alternatively, the primary remote station 16A can instruct the robot to transmit the audio and visual information to the primary 16A, and the secondary 16B and 16C remote stations. It being understood that each remote station 16A, 16B and 16C has a unique network identifier such as an IP address that allows the robot to direct information to each station. The packets may contain a BROADCAST field that contains the station IDs for the remote stations that are to receive packets from the robot. The BROADCAST field may be filled by the primary station 16A.

The active plus observational mode allows for training through the robot. For example, the primary remote station 16A may be operated by a nurse who moves the robot into visual and audio contact with a patient. The secondary remote stations 16B an 16C may be manned by personnel that observe and receive instructional training on providing care giving to the patient. Although instruction of medical personnel is described, the system can be used to train any group of users that are remotely located from a training area. For example, the system may be used to train personnel at a department store.

Figure 10:
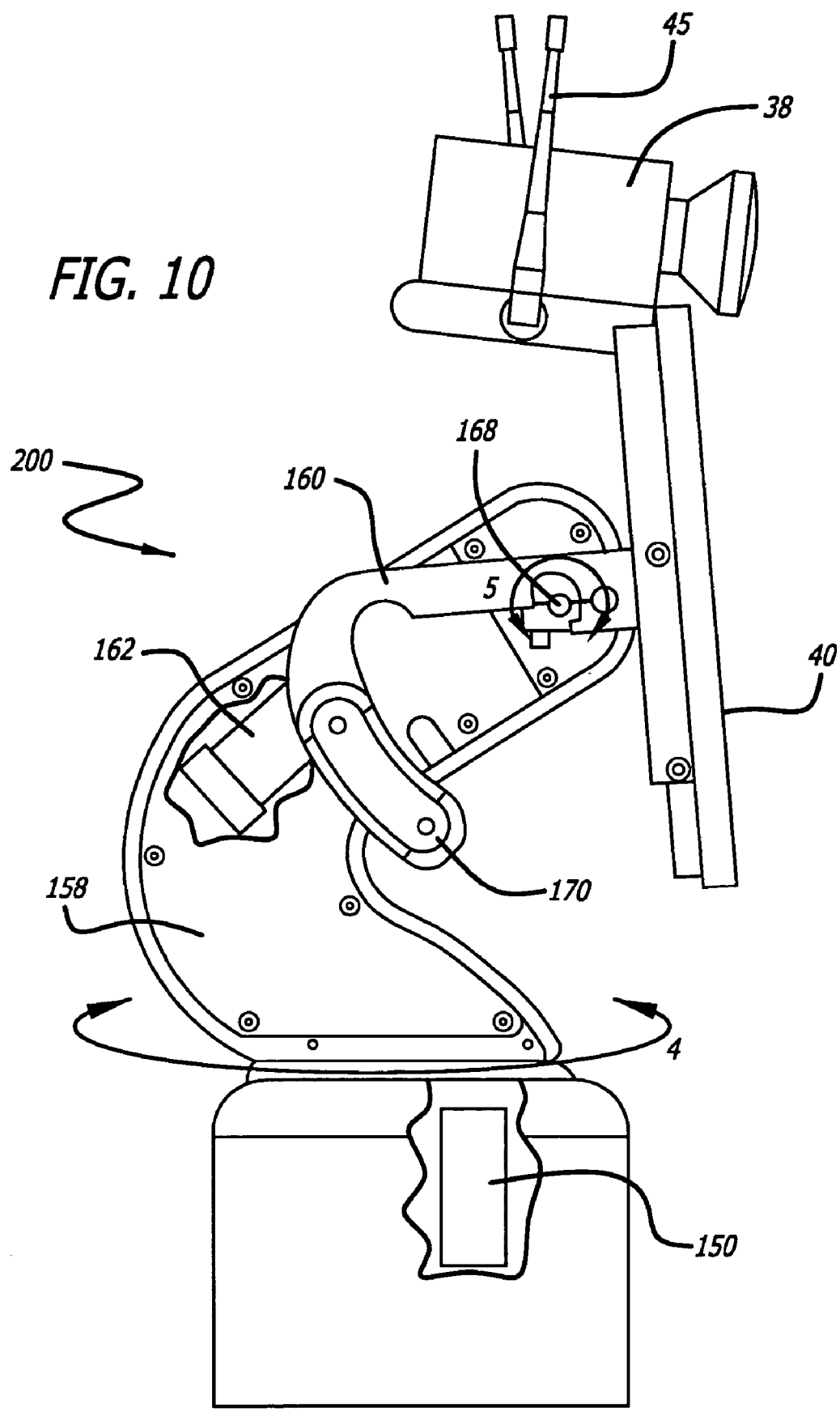
FIG. 10 is a side view of a robot head.

FIG. 10 shows a robot head 200 that can both pivot and spin the camera 38 and the monitor 40. The robot head 200 can be similar to the robot 12 but without the platform 110. The robot head 200 may have the same mechanisms and parts to both pivot the camera 38 and monitor 40 about the pivot axis 4, and spin the camera 38 and monitor 40 about the spin axis 5. The pivot axis may intersect the spin axis. Having a robot head 200 that both pivots and spins provides a wide viewing area. The robot head 200 may be in the system either with or instead of the mobile robot 12.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A mobile robot system, comprising:
a mobile robot that can move across a surface, said mobile robot has a monitor and a camera that captures a video image, said monitor and camera move together in at least one degree of freedom;
a first remote station that has a first monitor and an input device that receives input to cause movement of said mobile robot, said first monitor displays the video image, said first remote station being separate from said mobile robot; and,
a second remote station that has a second monitor that also displays the video image, said second remote station being separate from said mobile robot.

2. The system of claim 1, wherein said first remote station receives the video image from said mobile robot, and retransmits the video image to said second remote station.

3. The system of claim 1, wherein said mobile robot broadcast the video image to said first and second remote stations.

4. The system of claim 1, wherein said mobile robot has a microphone, and said first and second remote stations each have a speaker that receive a sound from said microphone.

5. The system of claim 1, wherein said mobile robot includes a monitor and a speaker, and said first remote station includes a camera and a microphone.

6. The system of claim 1, wherein said mobile robot includes a platform that provides three degrees of freedom.

7. The system of claim 1, further comprising a base station wirelessly coupled to said mobile robot.

8. A mobile robot system, comprising:
a mobile robot that can move across a surface, has a monitor and a camera that capture a video image, said monitor and camera move together in at least one degree of freedom;
first remote station means for controlling movement of said mobile robot and displaying the video image, said first remote station means being separate from said mobile robot; and,
second remote station means for displaying the video image, said second remote station means being separate from said mobile robot.

9. The system of claim 8, wherein said first remote station means receives the video image from said mobile robot, and retransmits the video image to said second remote station means.

10. The system of claim 8, wherein said mobile robot broadcast the video image to said first and second remote stations means.

11. The system of claim 8, wherein said mobile robot has a microphone, and said first and second remote station means each emit a sound provided by said microphone.

12. The system of claim 8, wherein said mobile robot includes a monitor and a speaker, and said first remote station means includes a camera and a microphone.

13. The system of claim 8, wherein said mobile robot includes a platform that provides three degrees of freedom.

14. The system of claim 8, further comprising a base station wirelessly coupled to said mobile robot.

15. A method for operating a mobile robot, comprising:
controlling movement of a mobile robot across a surface through a first remote station that is separate from the mobile robot, the mobile robot having a monitor and a camera that captures a video image, said monitor and camera move together in at least one degree of freedom;
displaying the video image at the first remote station and a second remote station that is separate from the mobile robot.

16. The method of claim 15, wherein the first remote station receives and retransmits the video image to the second remote station.

17. The method of claim 15, wherein the mobile robot broadcast the video image to the first and second remote stations.

18. The method of claim 15, further comprising generating a sound at the first and second remote stations that is provided by the mobile robot.

19. A mobile robot system, comprising:
a broadband network;
a mobile robot that can move across a surface, said mobile robot being coupled to said broadband network and has a monitor and camera that captures a video image, said monitor and a camera move together in at least one degree of freedom;
a first remote station that is coupled to said broadband network, said first remote station has a first monitor and an input device that receives input to cause movement of said mobile robot, said first monitor displays the video image from said camera, said first remote station being separate from said mobile robot; and,
a second remote station that is coupled to said broadband network and has a second monitor that also displays the video image, said second remote station being separate from said mobile robot.

20. The system of claim 19, wherein said first remote station receives the video image from said mobile robot through said broadband network, and retransmits the video image to said second remote station.

21. The system of claim 19, wherein said mobile robot broadcast the video image to said first and second remote stations through said broadband network.

22. The system of claim 19, wherein said mobile robot has a microphone, and said first and second remote stations each have a speaker that receive a sound from said microphone transmitted through said broadband network.

23. The system of claim 19, wherein said mobile robot includes a monitor and a speaker, and said first remote station includes a camera and a microphone.

24. The system of claim 19, wherein said mobile robot includes a platform that provides three degrees of freedom.

25. The system of claim 19, further comprising a base station that is coupled to said broadband network and wirelessly coupled to said mobile robot.

26. A mobile robot system, comprising: a broadband network;
a mobile robot that is coupled to said broadband network and has a monitor and a camera that captures a video image, said monitor and camera move together in at least one degree of freedom, that is transmitted through said broadband network;
first remote station means for controlling movement of said mobile robot and displaying the video image transmitted through said broadband network, said first remote station means being separate from said mobile robot; and,
second remote station means for displaying the video image, said second remote station means being separate from said mobile robot.

27. The system of claim 26, wherein said first remote station means receives the video image from said mobile robot, and retransmits the video image to said second remote station.

28. The system of claim 26, wherein said mobile robot broadcast the video image to said first and second remote stations means.

29. The system of claim 26, wherein said mobile robot has a microphone, and said first and second remote station means each emit a sound provided by said microphone transmitted through said broadband network.

30. The system of claim 26, wherein said mobile robot includes a monitor and a speaker, and said first remote station means includes a camera and a microphone.

31. The system of claim 26, wherein said mobile robot includes a platform that provides three degrees of freedom.

32. The system of claim 26, further comprising a base station that is coupled to said broadband network and is wirelessly coupled to said mobile robot.

33. A method for operating a mobile robot, comprising:
controlling movement of a mobile robot across a surface through a first remote station and a broadband network, the mobile robot having a monitor and a camera that captures a video image, said monitor and camera move together in at least one degree of freedom, the first remote station being separate from the mobile robot;
transmitting the video image through the broadband network; and,
displaying the video image at the first remote station and a second remote station that is separate from the mobile robot.

34. The method of claim 33, wherein the first remote station receives and retransmits the video image to the second remote station.

35. The method of claim 33, wherein the mobile robot broadcast the video image to the first and second remote stations.

36. The method of claim 33, further comprising generating a sound at the first and second remote stations that is provided by the mobile robot.

* * * * *